(12) United States Patent
Akagane

(10) Patent No.: US 9,184,373 B2
(45) Date of Patent: Nov. 10, 2015

(54) MANUFACTURING METHOD OF AN ULTRASONIC GENERATING DEVICE, AND MANUFACTURING METHOD OF AN ULTRASONIC TREATMENT DEVICE

(71) Applicant: OLYMPUS CORPORATION, Tokyo (JP)

(72) Inventor: Tsunetaka Akagane, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 13/837,681

(22) Filed: Mar. 15, 2013

(65) Prior Publication Data
US 2013/0274637 A1 Oct. 17, 2013

Related U.S. Application Data

(63) Continuation of application No. PCT/JP2012/070555, filed on Aug. 10, 2012.

(60) Provisional application No. 61/525,502, filed on Aug. 19, 2011.

(51) Int. Cl.
*H04R 17/00* (2006.01)
*H01L 41/25* (2013.01)
(Continued)

(52) U.S. Cl.
CPC ........ *H01L 41/25* (2013.01); *A61B 17/320068* (2013.01); *A61B 17/320092* (2013.01);
(Continued)

(58) Field of Classification Search
CPC ............... A61B 17/320068; A61B 17/320092; A61B 2017/00526; B06B 1/0611; B06B 1/0651; B06B 3/02; H01L 41/25; H01L 41/277; Y10T 29/42; Y10T 29/49005; Y10T 29/4908

USPC ................. 29/25.35, 592.1, 593, 594, 602.1, 29/609.1; 310/323, 325, 328, 348; 601/2; 604/22; 606/169–171

See application file for complete search history.

(56) References Cited

U.S. PATENT DOCUMENTS 5,371,429 A 12/1994 Manna
7,273,483 B2 * 9/2007 Wiener et al. .................. 606/169
(Continued)

FOREIGN PATENT DOCUMENTS

EP 0 875 301 A2 11/1998
JP A-2002-542690 12/2002
(Continued)

OTHER PUBLICATIONS

Jan. 15, 2015 Extended European Search Report issued in European Application No. 12826343.1.
(Continued)

*Primary Examiner* — Paul D Kim
(74) *Attorney, Agent, or Firm* — Oliff PLC

(57) ABSTRACT

A manufacturing method of an ultrasonic generating device includes calculating performance value based on a first electromechanical coupling factor in thickness directions and a second electromechanical coupling factor in diametrical directions for each of existing piezoelectric elements, calculating, for each of temporary conditions, a temporary influence value on the basis of a deviation of temporary amplitude of the ultrasonic vibrations, generated by the supply of the current having the predetermined current value, from a target amplitude in a target condition. The manufacturing method includes selecting the corresponding mounted piezoelectric element to be mounted on each of the element mounting portions from the existing piezoelectric elements so that the sum of actual influence values of all the element mounting portions is within a predetermined range with respect to the target amplitude.

7 Claims, 11 Drawing Sheets

(51) Int. Cl.
   *A61B 17/32*   (2006.01)
   *H01L 41/277*  (2013.01)
   *A61N 7/00*    (2006.01)
   *B06B 1/06*    (2006.01)
   *B06B 3/02*    (2006.01)
   *A61B 17/00*   (2006.01)

(52) U.S. Cl.
   CPC ............... *A61N7/00* (2013.01); *B06B 1/0611* (2013.01); *H01L 41/277* (2013.01); *A61B 2017/00526* (2013.01); *B06B 1/0651* (2013.01); *B06B 3/02* (2013.01); *Y10T 29/42* (2015.01); *Y10T 29/49004* (2015.01)

(56) References Cited

U.S. PATENT DOCUMENTS

| | | | |
|---|---|---|---|
| 8,531,064 B2 * | 9/2013 | Robertson et al. | 310/50 |
| 8,663,220 B2 * | 3/2014 | Wiener et al. | 606/42 |

| | | | |
|---|---|---|---|
| 2004/0008241 A1 | 1/2004 | Junhua | |
| 2006/0103264 A1 | 5/2006 | Junhua | |
| 2006/0256166 A1 | 11/2006 | Junhua | |
| 2009/0318944 A1 | 12/2009 | Kimura et al. | |
| 2010/0010395 A1 | 1/2010 | Gagnepain et al. | |
| 2010/0198070 A1 | 8/2010 | Asafusa et al. | |

FOREIGN PATENT DOCUMENTS

| | | |
|---|---|---|
| JP | A-2004-048985 | 2/2004 |
| JP | A-2009-227534 | 10/2009 |
| JP | A-2010-000336 | 1/2010 |
| WO | WO 2009/008282 A1 | 1/2009 |

OTHER PUBLICATIONS

Oct. 9, 2012 International Search Report issued in International Application No. PCT/JP2012/070555 (with translation).

Jun. 26, 2015 Office Action issued in European Application No. 12826343.1.

* cited by examiner

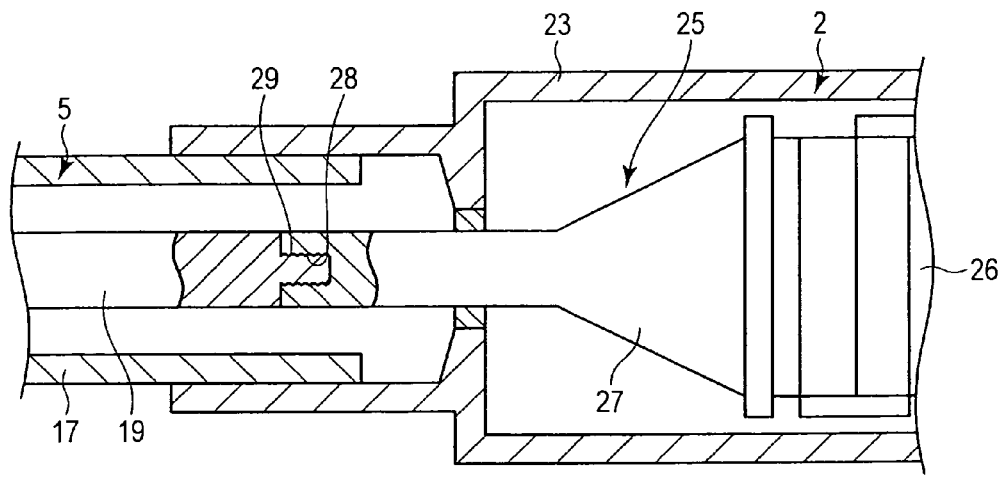
F I G. 2
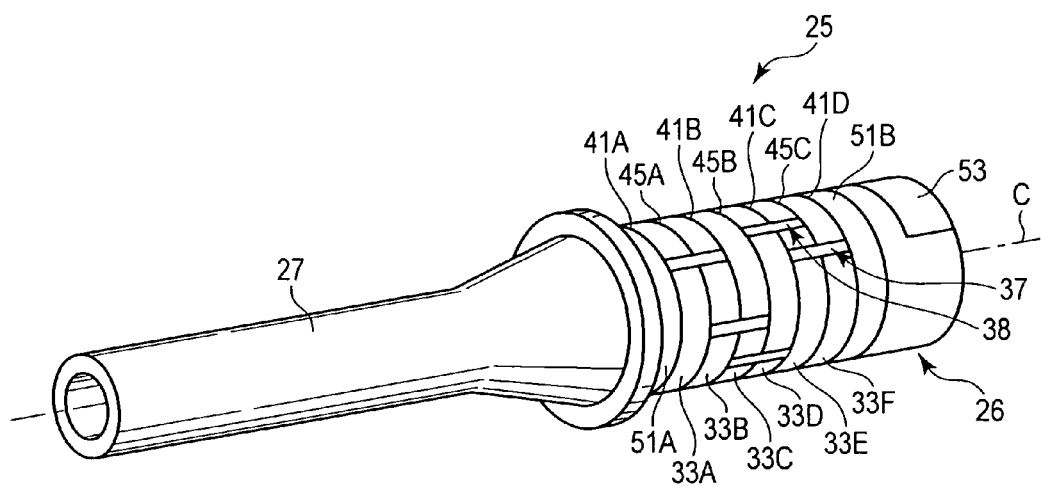
F I G. 3

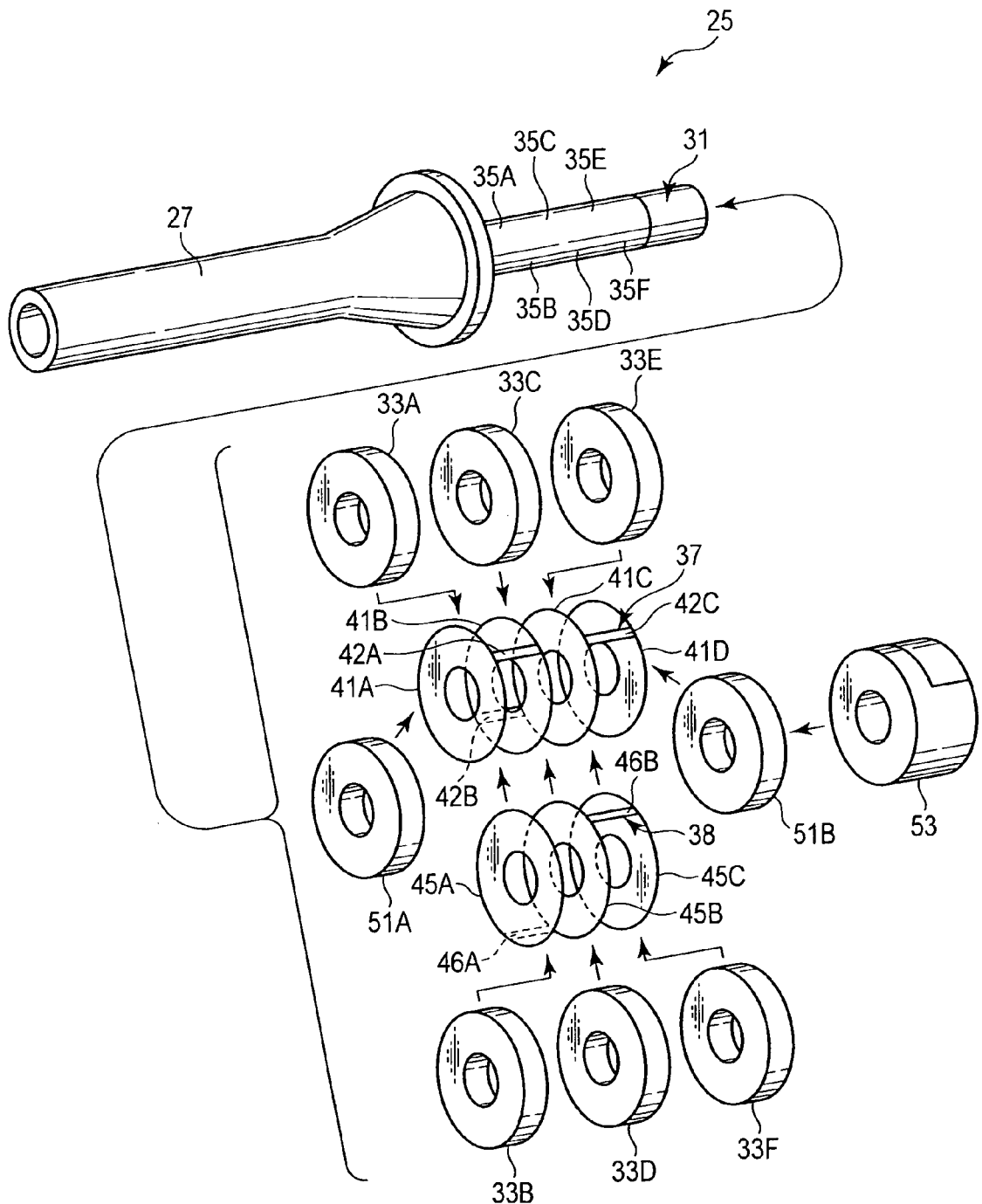
F I G. 4

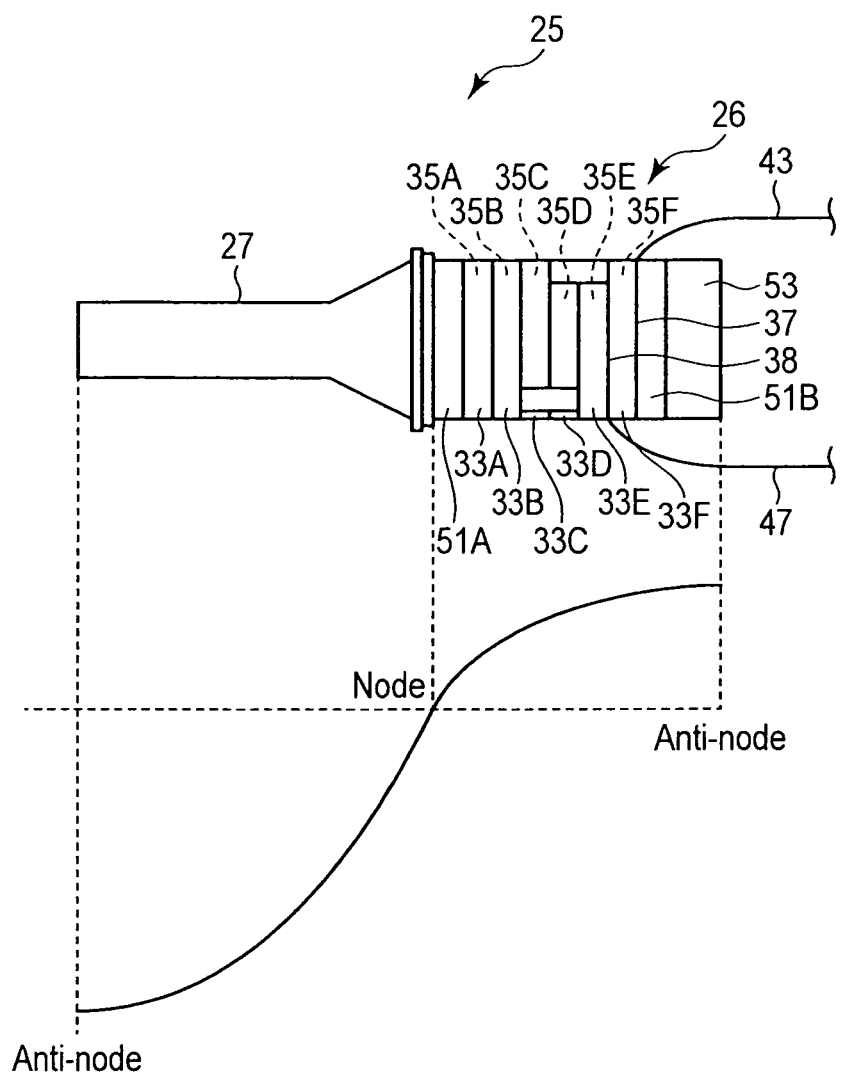
F I G. 5

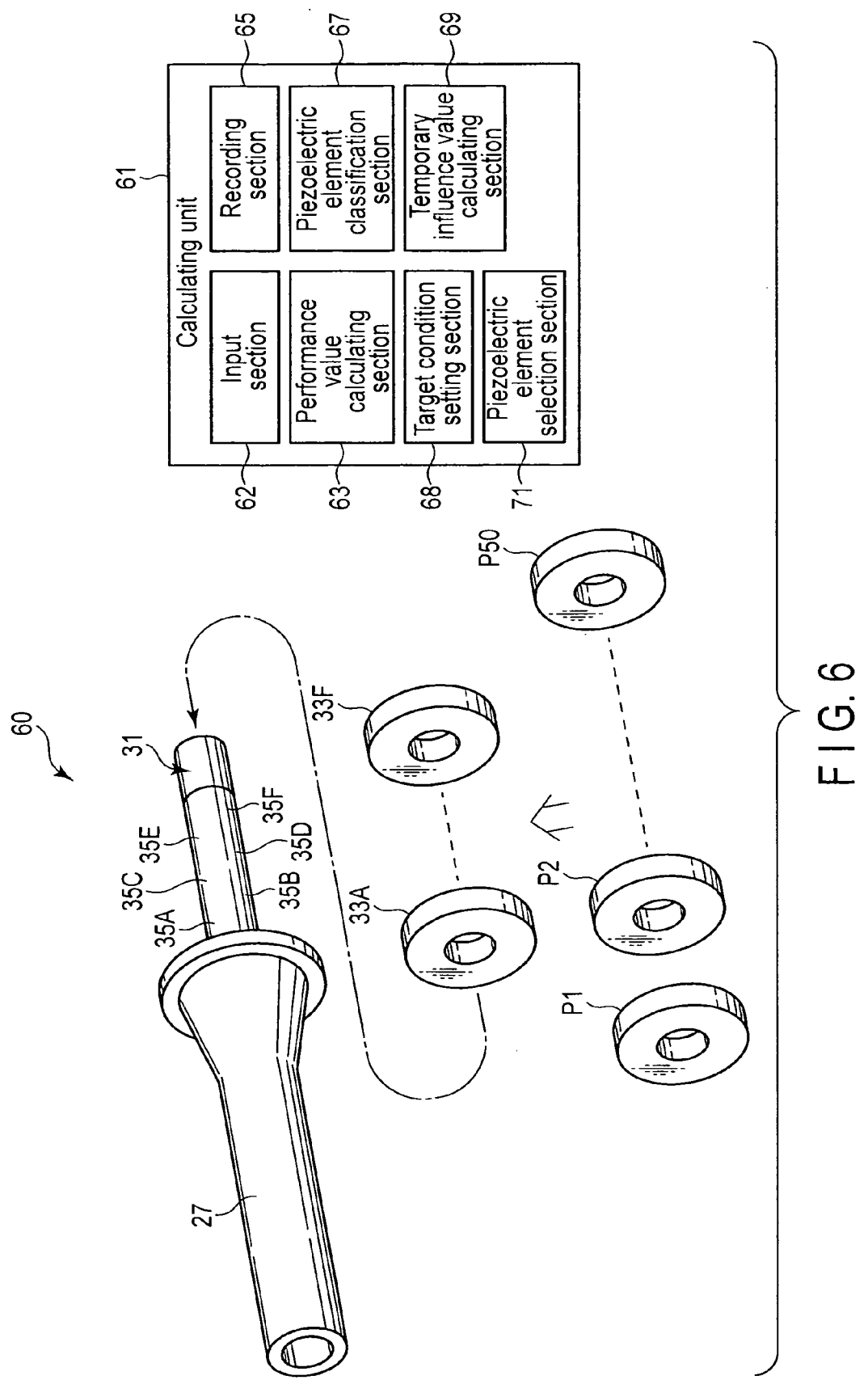
F I G. 6

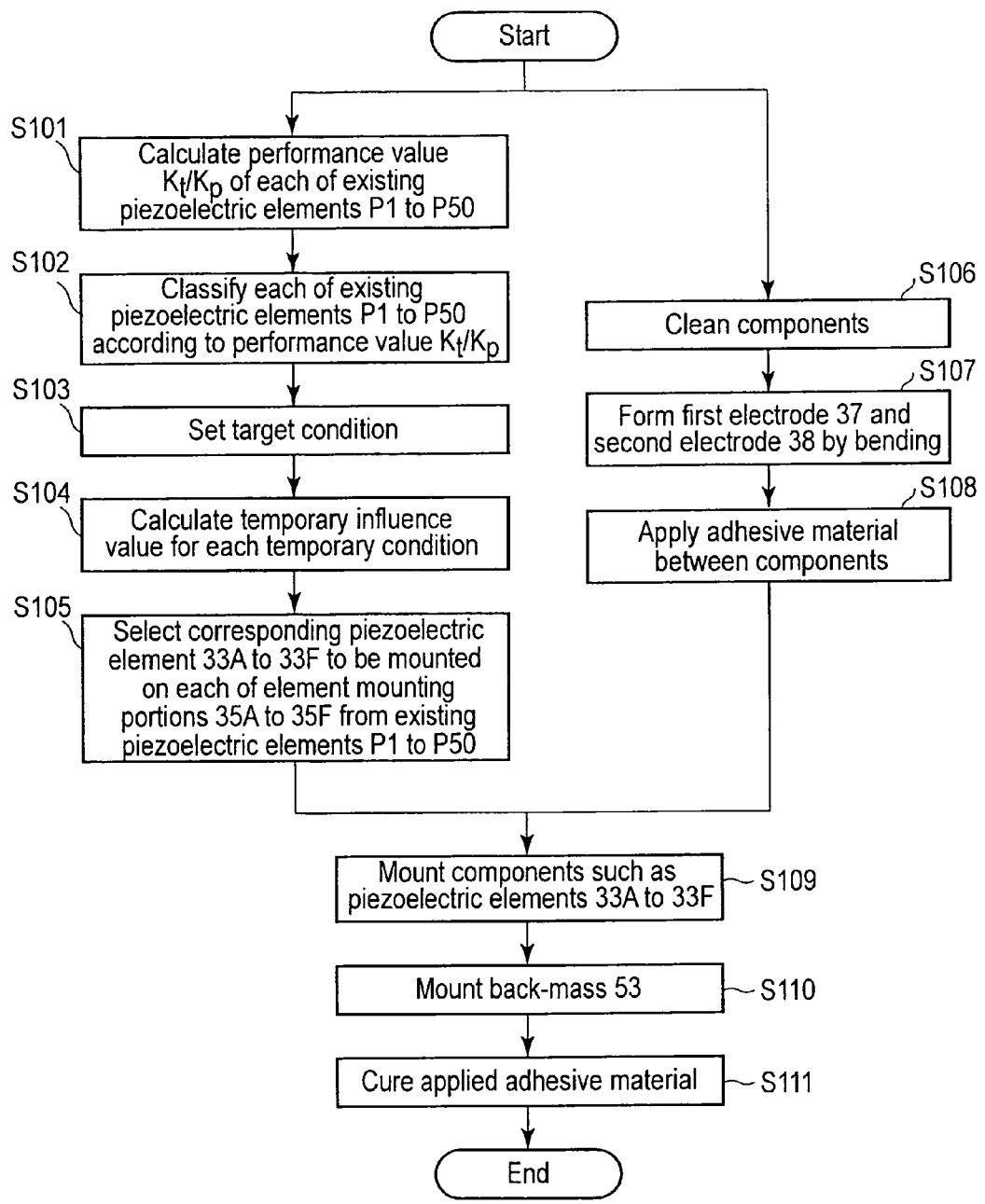
F I G. 7

|  | Element mounting portion | | | | | |
|---|---|---|---|---|---|---|
| | | 35A | 35B | 35C | 35D | 35E | 35F |
| Performance value $K_t/K_p$ | 0.735 | −3.341 | −3.124 | −2.906 | −2.689 | −2.471 | −2.254 |
| | 0.74 | −3.084 | −2.883 | −2.683 | −2.482 | −2.281 | −2.08 |
| | 0.745 | −2.827 | −2.643 | −2.459 | −2.275 | −2.091 | −1.907 |
| | 0.75 | −2.57 | −2.403 | −2.235 | −2.068 | −1.901 | −1.734 |
| | 0.755 | −2.313 | −2.162 | −2.012 | −1.861 | −1.711 | −1.56 |
| | 0.76 | −2.056 | −1.922 | −1.788 | −1.655 | −1.521 | −1.387 |
| | 0.765 | −1.799 | −1.682 | −1.565 | −1.448 | −1.331 | −1.214 |
| | 0.77 | −1.542 | −1.442 | −1.341 | −1.241 | −1.141 | −1.04 |
| | 0.775 | −1.285 | −1.201 | −1.118 | −1.034 | −0.95 | −0.867 |
| | 0.78 | −1.028 | −0.961 | −0.894 | −0.827 | −0.76 | −0.693 |
| | 0.785 | −0.771 | −0.721 | −0.671 | −0.62 | −0.57 | −0.52 |
| | 0.79 | −0.514 | −0.481 | −0.447 | −0.414 | −0.38 | −0.347 |
| | 0.795 | −0.257 | −0.24 | −0.224 | −0.207 | −0.19 | −0.173 |
| | 0.8 | 0 | 0 | 0 | 0 | 0 | 0 |
| | 0.805 | 0.257 | 0.24 | 0.224 | 0.207 | 0.19 | 0.173 |
| | 0.81 | 0.514 | 0.481 | 0.447 | 0.414 | 0.38 | 0.347 |
| | 0.815 | 0.771 | 0.721 | 0.671 | 0.62 | 0.57 | 0.52 |
| | 0.82 | 1.028 | 0.961 | 0.894 | 0.827 | 0.76 | 0.693 |
| | 0.825 | 1.285 | 1.201 | 1.118 | 1.034 | 0.95 | 0.867 |
| | 0.83 | 1.542 | 1.442 | 1.341 | 1.241 | 1.141 | 1.04 |
| | 0.835 | 1.799 | 1.682 | 1.565 | 1.448 | 1.331 | 1.214 |
| | 0.84 | 2.056 | 1.922 | 1.788 | 1.655 | 1.521 | 1.387 |
| | 0.845 | 2.313 | 2.162 | 2.012 | 1.861 | 1.711 | 1.56 |
| | 0.85 | 2.57 | 2.403 | 2.235 | 2.068 | 1.901 | 1.734 |
| | 0.855 | 2.827 | 2.643 | 2.459 | 2.275 | 2.091 | 1.907 |
| | 0.86 | 3.084 | 2.883 | 2.683 | 2.482 | 2.281 | 2.08 |
| | 0.865 | 3.341 | 3.124 | 2.906 | 2.689 | 2.471 | 2.254 |

F I G. 9

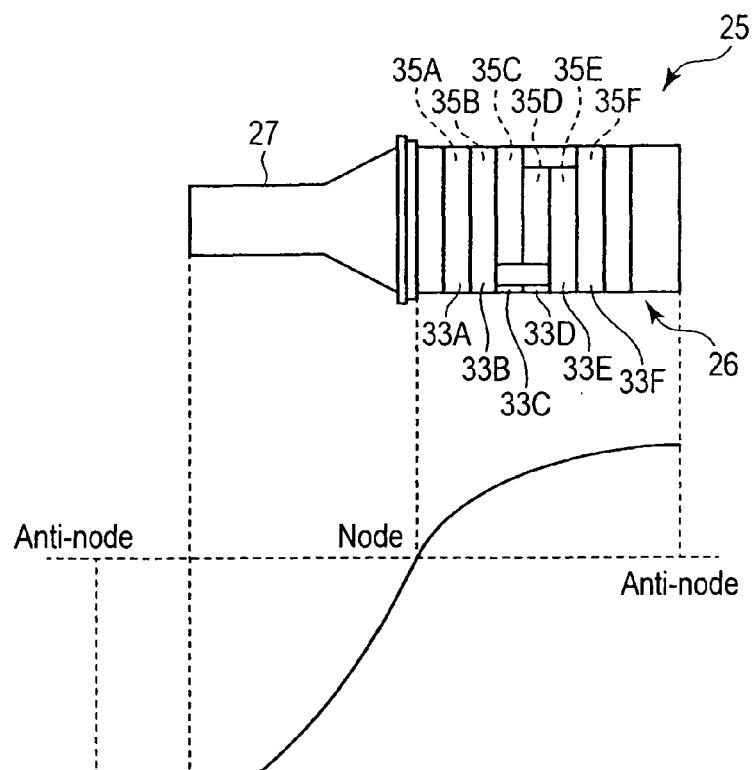
F I G. 10
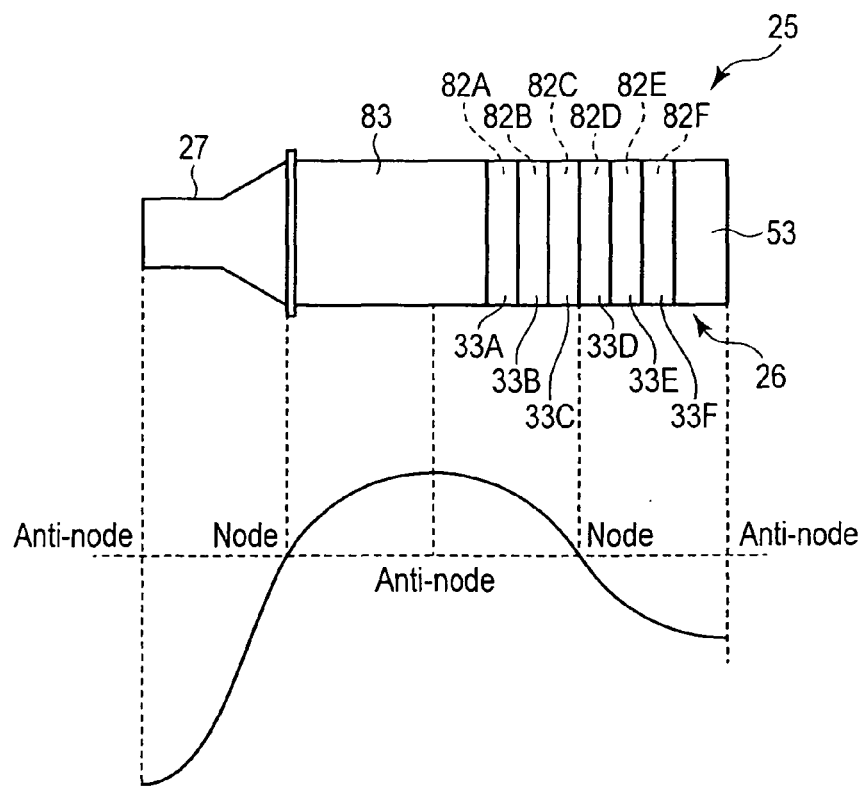
F I G. 11

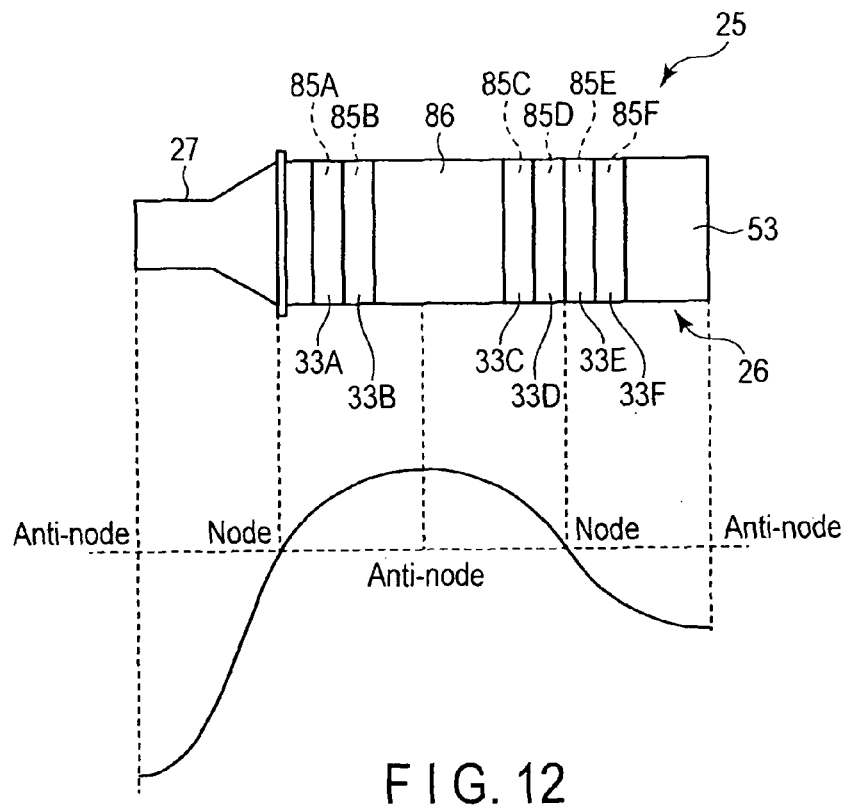
F I G. 12
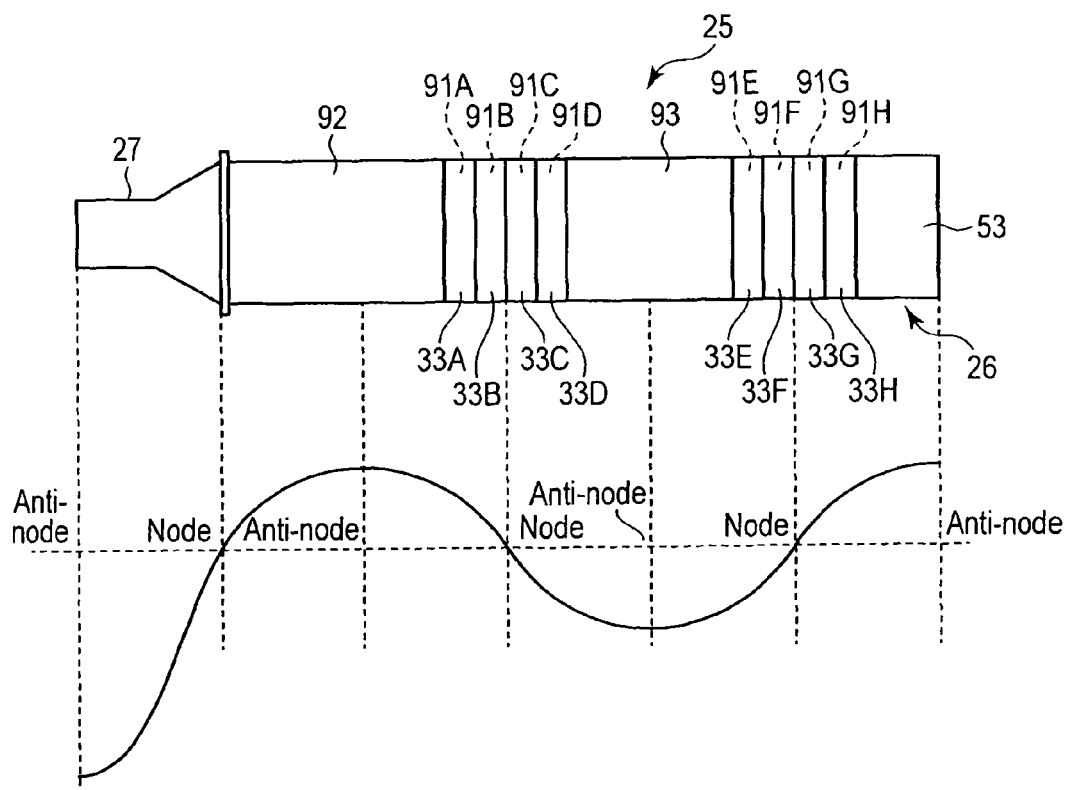
F I G. 13

MANUFACTURING METHOD OF AN ULTRASONIC GENERATING DEVICE, AND MANUFACTURING METHOD OF AN ULTRASONIC TREATMENT DEVICE

CROSS-REFERENCE TO RELATED APPLICATIONS

This is a Continuation application of PCT Application No. PCT/JP2012/070555, filed Aug. 10, 2012 and based upon and claiming the benefit of priority from prior U.S. Provisional Application No. 61/525,502, filed Aug. 19, 2011, the entire contents of which are incorporated herein by reference.

BACKGROUND OF THE INVENTION

1. Field of the Invention

The present invention relates to an ultrasonic generating device configured to generate ultrasonic vibrations when supplied with a current, and an ultrasonic treatment device including the ultrasonic generating device. The present invention also relates to a manufacturing method of the ultrasonic generating device and a manufacturing method of the ultrasonic treatment device.

2. Description of the Related Art

An ultrasonic surgery device (ultrasonic treatment device) disclosed in Jpn. Pat. Appln. KOKAI Publication No. 2010-000336 includes an ultrasonic generating device (ultrasonic vibrator unit) including an ultrasonic vibrator which formed from a plurality of piezoelectric elements, and a probe which is connected to the ultrasonic vibrator unit and which is configured to transmit ultrasonic vibrations generated in the ultrasonic vibrator (ultrasonic oscillator), the probe being configured to treat a living tissue by a treatment portion formed at a distal end portion thereof. When a predetermined constant current is supplied to the ultrasonic vibrator from a power supply unit, this ultrasonic surgery device is configured to ultrasonically vibrate the probe (treatment portion) with constant amplitude. That is, the ultrasonic vibrator is driven by constant current control, and the constant amplitude of the ultrasonic vibrations in the probe (treatment portion) is maintained.

BRIEF SUMMARY OF THE INVENTION

According to one aspect of the invention, a manufacturing method of an ultrasonic generating device, the manufacturing method including that calculating performance value based on a first electromechanical coupling factor in thickness directions and a second electromechanical coupling factor in diametrical directions for each of existing piezoelectric elements; setting a target condition where ultrasonic vibrations having target amplitude are generated when a corresponding reference piezoelectric element having the performance value equal to a reference value is mounted on each of a plurality of element mounting portions located at positions different from one another in a transmission direction of the ultrasonic vibrations and when a current having a predetermined current value is supplied; calculating, for each of temporary conditions, a temporary influence value on the basis of a deviation of temporary amplitude of the ultrasonic vibrations, generated by the supply of the current having the predetermined current value, from the target amplitude in the target condition, a temporary piezoelectric element having the performance value different from the reference value being mounted on only one element mounting portion instead of the reference piezoelectric element in each of the temporary conditions as compared with the target condition, the temporary conditions being set for each of the element mounting portions on which the temporary piezoelectric element is mounted and for each of the performance values of the temporary piezoelectric elements; selecting the corresponding mounted piezoelectric element to be mounted on each of the element mounting portions from the existing piezoelectric elements so that the sum of actual influence values of all the element mounting portions is within a predetermined range with respect to the target amplitude, when the temporary influence value in the corresponding temporary condition, in which the temporary piezoelectric element having the same performance value as the mounted piezoelectric element to be actually mounted is mounted, is used as the actual influence value in each of the element mounting portions; and mounting the selected corresponding mounted piezoelectric elements on each of the element mounting portions so that the thickness directions thereof are parallel to the transmission direction of the ultrasonic vibrations and so that the diametrical directions thereof are perpendicular to the transmission direction of the ultrasonic vibrations.

According to one another aspect of invention, an ultrasonic generating device includes that a plurality of element mounting portions located at positions different from one another in a transmission direction of ultrasonic vibrations; and a plurality of mounted piezoelectric elements each of which has a performance value based on a first electromechanical coupling factor in the thickness directions and a second electromechanical coupling factor in the diametrical directions, each of the mounted piezoelectric elements being mounted on the corresponding element mounting portion so that the thickness directions are parallel to the transmission direction of the ultrasonic vibrations and so that the diametrical directions are perpendicular to the transmission direction of the ultrasonic vibrations, wherein each of the mounted piezoelectric elements is selected from existing piezoelectric elements so that a sum of actual influence values of all the element mounting portions is within a predetermined range with respect to the target amplitude, in a case of being set a target condition where the ultrasonic vibrations having the target amplitude are generated when a corresponding reference piezoelectric element having the performance value equal to a reference value is mounted on each of the element mounting portions and when a current having a predetermined current value is supplied, in a case of calculating, for each of temporary conditions, a temporary influence value on the basis of a deviation of temporary amplitude of the ultrasonic vibrations, generated by the supply of the current having the predetermined current value, from the target amplitude in the target condition, a temporary piezoelectric element having the performance value different from the reference value is mounted on only one element mounting portion instead of the reference piezoelectric element in each of the temporary conditions as compared with the target condition, the temporary conditions being set for each of the element mounting portions on which the temporary piezoelectric element is mounted and for each of the performance values of the temporary piezoelectric elements, and in a case of using the temporary influence value in the corresponding temporary condition, in which the temporary piezoelectric element having the same performance value as the mounted piezoelectric element is mounted, as the actual influence value in each of the element mounting portions.

According to one another aspect of the invention, a manufacturing method of an ultrasonic generating device, the manufacturing method including that calculating performance value based on a first electromechanical coupling factor in thickness directions and a second electromechanical coupling factor in diametrical directions for each of piezoelectric elements; setting, as a target amplitude, amplitude of ultrasonic vibrations generated when the corresponding piezoelectric element having the performance value to be a reference value is mounted on each of a plurality of element mounting portions, the element mounting portions being located at positions different from one another in a transmission direction of the ultrasonic vibrations; calculating an influence value with respect to the target amplitude for each of the element mounting portions and for each of performance values; selecting the corresponding piezoelectric element to be mounted on each of the element mounting portions from all the piezoelectric elements so that a sum of the influence values of all the element mounting portions is within a predetermined range with respect to the target amplitude; and mounting the selected corresponding piezoelectric element on each of the element mounting portions so that the thickness directions are parallel to the transmission direction of the ultrasonic vibrations and so that the diametrical directions are perpendicular to the transmission direction of the ultrasonic vibrations.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic sectional view showing the configurations of an ultrasonic transducer, a sheath, and a probe of the ultrasonic treatment device according to the first embodiment;

FIG. 3 is a schematic perspective view showing an ultrasonic generating device according to the first embodiment;

FIG. 4 is a schematic perspective view showing the ultrasonic generating device according to the first embodiment which is disassembled into components;

FIG. 5 is a schematic diagram showing the ultrasonic generating device according to the first embodiment;

FIG. 6 is a schematic diagram showing an ultrasonic adjusting device used in the manufacture of the ultrasonic generating device according to the first embodiment;

FIG. 7 is a flowchart showing a manufacturing method of the ultrasonic generating device according to the first embodiment;

FIG. 9 is a schematic diagram showing temporary influence value in each of the temporary conditions of the ultrasonic generating device according to the first embodiment;

FIG. 10 is a schematic diagram showing an ultrasonic generating device according to a first modification of the first embodiment;

FIG. 11 is a schematic diagram showing an ultrasonic generating device according to a second modification of the first embodiment;

FIG. 12 is a schematic diagram showing an ultrasonic generating device according to a third modification of the first embodiment;

FIG. 13 is a schematic diagram showing an ultrasonic generating device according to a fourth modification of the first embodiment.

DETAILED DESCRIPTION OF THE INVENTION

First Embodiment

Figure 1:
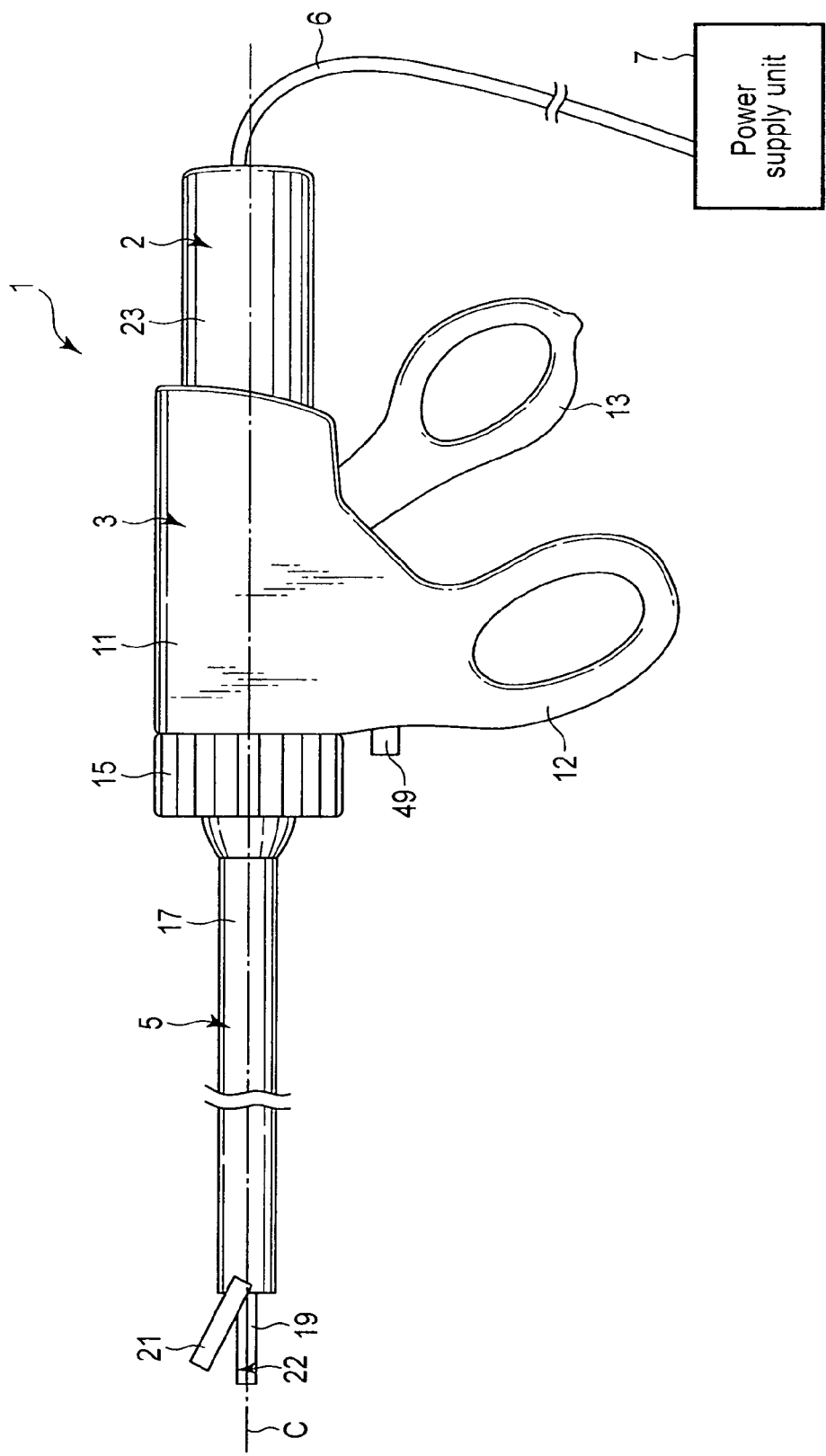
FIG. 1 is a schematic diagram showing an ultrasonic treatment device according to a first embodiment of the present invention.

A first embodiment of the present invention is described with reference to FIG. 1 to FIG. 9. FIG. 1 is a diagram showing an ultrasonic treatment device (ultrasonic surgical device) 1 according to the present embodiment. As shown in FIG. 1, the ultrasonic treatment device 1 includes an ultrasonic transducer 2, a handle unit 3 to which the ultrasonic transducer 2 is coupled from a proximal direction side, and a treatment unit 5 coupled to the handle unit 3 from a distal direction side. One end of a cable 6 is connected to the ultrasonic transducer 2. The other end of the cable 6 is connected to a power supply unit 7.

The handle unit 3 includes a cylindrical case 11, a fixed handle 12 formed integrally with the cylindrical case 11, and a movable handle 13 configured to open/close relative to the fixed handle 12. A rotational operation knob 15 is provided to the distal direction side of the cylindrical case 11. The rotational operation knob 15 is attached to the cylindrical case 11 rotatably around a longitudinal axis C.

The ultrasonic transducer 2 is inserted into the handle unit 3 from the proximal direction side, and is coupled to the cylindrical case 11 of the handle unit 3. The treatment unit 5 includes a sheath 17 extending along the longitudinal axis C from the inside of the handle unit 3 toward the distal direction. The distal end of the sheath 17 is located to the distal direction side of the rotational operation knob 15. That is, the sheath 17 is provided to project from the rotational operation knob 15 toward the distal direction.

The treatment unit 5 includes a probe 19 configured to be inserted through the sheath 17. The probe 19 is supported by the sheath 17 via a support member (not shown). A distal end of the probe 19 is located to the distal direction side of the distal end of the sheath 17. That is, the probe 19 is provided to project from the distal end of the sheath 17 toward the distal direction. The sheath 17 and the probe 19 are inserted into the handle unit 3. Inside the handle unit 3, the sheath 17 is coupled to the rotational operation knob 15 of the handle unit 3. Inside the handle unit 3, the sheath 17 and the probe 19 are also coupled to the ultrasonic transducer 2.

A jaw 21 is coupled to a distal end portion of the sheath 17. The jaw 21 is rotatable relative to the sheath 17 around a portion coupled to the sheath 17. The jaw 21 rotates relative to the sheath 17, and thereby opens/closes relative to a distal end portion of the probe 19. A living tissue can be grasped between the distal end portion of the probe 19 and the jaw 21 by the open/close motion of the jaw 21. The sheath 17, the probe 19, and the jaw 21 are rotatable relative to the cylindrical case 11 around the longitudinal axis C together with the rotational operation knob 15.

FIG. 2 is a diagram showing the configurations of the ultrasonic transducer 2, the sheath 17, and the probe 19. As shown in FIG. 2, the ultrasonic transducer 2 includes a vibrator case 23, and an ultrasonic generating device (ultrasound generating device) 25 provided inside the vibrator case 23. The proximal end portion of the sheath 17 is fitted into the vibrator case 23 so that the vibrator case 23 is coupled to the sheath 17. The ultrasonic generating device 25 is coupled to the probe 19.

FIG. 3 to FIG. 5 are diagrams showing the configuration of the ultrasonic generating device 25. As shown in FIG. 3 to FIG. 5, the ultrasonic generating device 25 includes an ultrasonic vibrator (ultrasonic oscillator) 26 configured to generate ultrasonic vibrations when supplied with a current, and a horn 27 provided to the distal direction side of the ultrasonic vibrator 26. The amplitude of ultrasonic vibrations is increased by the horn 27. As shown in FIG. 2, an internal thread portion 28 is formed in a distal end portion of the horn 27. An external thread portion 29 is formed in a proximal end portion of the probe 19. The external thread portion 29 is threaded into the internal thread portion 28, and the ultrasound generating device 25 is thereby coupled to the probe 19.

When the probe 19 is coupled to the horn 27 of the ultrasonic generating device 25, the ultrasonic vibrations generated in the ultrasonic vibrator 26 are transmitted to the distal end of the probe 19 through (via) the horn 27 and the probe 19. That is, the ultrasonic vibrations are transmitted to the distal end from the proximal end in the probe 19 along the longitudinal axis C. At the same time, the distal end of the probe 19 and the proximal end of the ultrasonic generating device 25 are anti-node positions of the ultrasonic vibrations. The ultrasonic vibrations are longitudinal vibrations in which an transmission direction coincides with a vibration direction of the ultrasonic vibrations. The transmission direction and vibration direction of the ultrasonic vibration are parallel to the longitudinal axis C.

Frictional heat is generated between the distal end portion of the probe 19 and a living tissue such as a blood vessel by the ultrasonic vibrations of the probe 19 when the living tissue is grasped between the distal end portion of the probe 19 and the jaw 21. The living tissue is cut and coagulated between the distal end portion of the probe 19 and the jaw 21 by the generated frictional heat. As described above, the distal end portion of the probe 19 is a treatment portion 22 to which the ultrasonic vibrations generated by the ultrasonic generating device 25 are transmitted, and which is configured to conduct a treatment by using the transmitted ultrasonic vibrations.

As shown in FIG. 3 to FIG. 5, the ultrasonic generating device 25 is provided with a columnar portion 31 located to the proximal direction side of the horn 27 along the longitudinal axis C. The columnar portion 31 is provided integrally with the horn 27 or provided to be coupled to the proximal direction side of the horn 27.

The ultrasonic vibrator 26 of the ultrasonic generating device 25 includes a plurality of (six in the present embodiment) ring-shaped piezoelectric elements (mounted piezoelectric elements) 33A to 33F. A supplied current is converted to ultrasonic vibrations by piezoelectric elements 33A to 33F. The same number of element mounting portions 35A to 35F as piezoelectric elements 33A to 33F are formed in the columnar portion 31. Element mounting portions 35A to 35F are located at positions different from one another in a transmission direction of the ultrasonic vibrations. Each of the piezoelectric elements 33A to 33F is mounted on a corresponding element mounting portion 35A to 35F. For example, piezoelectric element 33A is mounted on the element mounting portion 35A. Each piezoelectric element 33A to 33F is mounted in a state that thickness directions are parallel to the transmission direction of the ultrasonic vibrations and in a state that diametrical directions are perpendicular to the transmission direction of the ultrasonic vibrations.

A first electrode 37 and a second electrode 38 are mounted on the columnar portion 31. The first electrode 37 includes a ring portion 41A located to the distal direction side of piezoelectric element 33A, a ring portion 41B located between piezoelectric element 33B and piezoelectric element 33C, a ring portion 41C located between piezoelectric element 33D and piezoelectric element 33E, and a ring portion 41D located to the proximal direction side of piezoelectric element 33F. The first electrode 37 also includes a link portion 42A which electrically connects the ring portion 41A and the ring portion 41B, a link portion 42B which electrically connects the ring portion 41B and the ring portion 41C, and a link portion 42C which electrically connects the ring portion 41C and the ring portion 41D. One end of an electrical signal line 43 is connected to the first electrode 37. The other end of electrical signal line 43 is connected to the power supply unit 7 through an inside of the cable 6.

The second electrode 38 includes a ring portion 45A located between piezoelectric element 33A and piezoelectric element 33B, a ring portion 45B located between piezoelectric element 33C and piezoelectric element 33D, and a ring portion 45C located between piezoelectric element 33E and piezoelectric element 33F. The second electrode 38 also includes a link portion 46A which electrically connects the ring portion 45A and the ring portion 45B, and a link portion 46B which electrically connects the ring portion 45B and the ring portion 45C. One end of an electrical signal line 47 is connected to the second electrode 38. The other end of electrical signal line 47 is connected to the power supply unit 7 through the inside of the cable 6.

As shown in FIG. 1, a button portion 49 is provided to the fixed handle 12 of the handle unit 3. The button portion 49 is electrically connected to the power supply unit 7 via, for example, an electrical signal line (not shown). When the button portion 49 is pressed, an electrical signal is input to the power supply unit 7. As a result, a current having a predetermined current value is supplied to piezoelectric elements 33A to 33F from the power supply unit 7 via electrical signal lines 43 and 47, the first electrode 37, and the second electrode 38. At the same time, the supplied current is converted to ultrasonic vibrations in each of piezoelectric elements 33A to 33F. Thereby, ultrasonic vibrations are generated in the ultrasonic vibrator 26.

When the ultrasonic vibrations are generated, a proximal end of the ultrasonic generating device 25 (a proximal end of the columnar portion 31) and a distal end of the ultrasonic generating device 25 (a distal end of the horn 27) are the anti-node positions (loop positions) of the ultrasonic vibrations. The dimension of the ultrasonic generating device 25 along the longitudinal axis C (in the transmission direction of the ultrasonic vibrations) is equal to half the wavelength of the ultrasonic vibrations. Among element mounting portions 35A to 35F, element mounting portion 35A is at the shortest distance from (closest to) the node position of the ultrasonic vibrations in the transmission direction of the ultrasonic vibrations. Among element mounting portions 35A to 35F, element mounting portion 35F is at the greatest distance from (farthest from) the node position of the ultrasonic vibrations in the transmission direction of the ultrasonic vibrations.

As shown in FIG. 3 to FIG. 5, insulating rings 51A and 51B are mounted on the columnar portion 31. The insulating ring 51A is located to the distal direction side of the ring portion 41A of the first electrode 37. The insulating ring 51B is located to the proximal direction side of the ring portion 41D of the first electrode 37. The insulating ring 51A is provided so that the current supplied from the power supply unit 7 is not transmitted toward the distal direction side from the insulating ring 51A. The insulating ring 51B is provided so that the current supplied from the power supply unit 7 is not transmitted toward the proximal direction side from the insulating ring 51B.

A back-mass 53 is also mounted on the columnar portion 31. The back-mass 53 is located to the proximal direction side of the insulating ring 51B. Piezoelectric elements 33A to 33F, the first electrode 37, the second electrode 38, and the insulating rings 51A and 51B are pressed toward the distal direction by the back-mass 53. As a result, piezoelectric elements 33A to 33F, the first electrode 37, the second electrode 38, and the insulating rings 51A and 51B are held between the horn 27 and the back-mass 53. Therefore, piezoelectric elements 33A to 33F, the first electrode 37, the second electrode 38, and the insulating rings 51A and 51B which are firmly fixed between the horn 27 and the back-mass 53 are mounted on the columnar portion 31.

Now, manufacturing methods of the ultrasonic generating device 25 and the ultrasonic treatment device 1 are described. FIG. 6 is a diagram showing an ultrasonic adjusting device (ultrasound adjusting device) 60 used in the manufacture of the ultrasonic generating device 25. The amplitude of ultrasonic vibrations generated by the ultrasonic generating device 25 is adjusted by the use of the ultrasonic adjusting device 60. As shown in FIG. 6, the ultrasonic adjusting device 60 includes the above-described piezoelectric elements 33A to 33F, and element mounting portions 35A to 35F in each of which a corresponding piezoelectric element 33A to 33F is mounted. The ultrasonic adjusting device 60 also includes a plurality of (50 in the present embodiment) existing piezoelectric elements P1 to P50 which are piezoelectric elements that exist during manufacture. Each of the piezoelectric elements (mounted piezoelectric elements) 33A to 33F to be mounted on the corresponding element mounting portion 35A to 35F is selected from existing piezoelectric elements P1 to P50.

Each of existing piezoelectric elements P1 to P50 has a first electromechanical coupling factor Kt in the thickness directions, and a second electromechanical coupling factor Kp in the diametrical directions. Here, the first electromechanical coupling factor Kt is a factor indicating the relation between electrical energy and vibrational energy in the thickness directions when a current is supplied to each of existing piezoelectric elements P1 to P50. The second electromechanical coupling factor Kp is a factor indicating the relation between electrical energy and vibrational energy in the diametrical directions when a current is supplied to each of existing piezoelectric elements P1 to P50.

Each of the piezoelectric elements 33A to 33F selected from existing piezoelectric elements P1 to P50 are mounted so that the thickness directions are parallel to the transmission direction of the ultrasonic vibrations and so that the diametrical directions are perpendicular to the transmission direction of the ultrasonic vibrations. Accordingly, the proportionality constant between the current value of the supplied current and the amplitude of the ultrasonic vibrations varies according to a value of the first electromechanical coupling factor Kt and a value of the second electromechanical coupling factor Kp of each of piezoelectric elements 33A to 33F. That is, the amplitude of the ultrasonic vibrations when a predetermined current is supplied varies in accordance with the value of the first electromechanical coupling factor Kt and the value of the second electromechanical coupling factor Kp of each of piezoelectric elements 33A to 33F.

As shown in FIG. 6, the ultrasonic adjusting device 60 includes a calculating unit 61 such as a computer. The calculating unit 61 includes an input section 62, a performance value calculating section 63, and a recording section 65. FIG. 7 is a flowchart showing the manufacturing method of the ultrasonic generating device 25. As shown in FIG. 7, when the ultrasonic generating device 25 is manufactured, the performance value of each of existing piezoelectric elements P1 to P50 is calculated by the performance value calculating section 63 (step S101). At the same time, a performance value based on the first electromechanical coupling factor Kt and the second electromechanical coupling factor Kp is calculated for each of existing piezoelectric elements P1 to P50. In the present embodiment, a performance value Kt/Kp is calculated on the basis of the first electromechanical coupling factor Kt and the second electromechanical coupling factor Kp for each of existing piezoelectric elements P1 to P50. As a modification, a performance value |Kt−Kp| or |Kt+Kp| or Kt×Kp may be calculated for each of existing piezoelectric elements P1 to P50.

When each of existing piezoelectric elements P1 to P50 is manufactured, it is not possible to set the first electromechanical coupling factor Kt in the thickness directions and the second electromechanical coupling factor Kp in the diametrical directions to desired values. Therefore, the first electromechanical coupling factor Kt in the thickness directions and the second electromechanical coupling factor Kp in the diametrical directions vary by each of the existing piezoelectric elements P1 to P50. Thus, the performance value Kt/Kp varies by each of the existing piezoelectric elements P1 to P50.

The first electromechanical coupling factor Kt and the second electromechanical coupling factor Kp of each of existing piezoelectric elements P1 to P50 are input by the input section 62. As a modification, the first electromechanical coupling factor Kt and the second electromechanical coupling factor Kp of each of existing piezoelectric elements P1 to P50 may be recorded in the recording section 65.

As shown in FIG. 6, the calculating unit 61 includes a piezoelectric element classification section 67. As shown in FIG. 7, existing piezoelectric elements P1 to P50 are classified according to the performance value Kt/Kp by the piezoelectric element classification section 67 (step S102). For example, the existing piezoelectric elements (for example, P3 and P33) having a performance value Kt/Kp that is 0.7875 or more and below 0.7925 are classified into a type having a performance value Kt/Kp of 0.79. The existing piezoelectric elements (for example, P10 and P41) having a performance value Kt/Kp that is 0.7925 or more and below 0.7975 are classified into a type having a performance value Kt/Kp of 0.795. In this way, existing piezoelectric elements P1 to P50 are classified into several types according to the performance value Kt/Kp.

The number of the existing piezoelectric elements (P1 to P50) belonging to each of the types is recorded in the recording section 65. For example, when the performance value Kt/Kp of existing piezoelectric elements P3 and P33 is 0.7875 or more and below 0.7925, the number of the existing piezoelectric elements (P1 to P50) belonging to the type having a performance value Kt/Kp of 0.79 is two.

As shown in FIG. 6, the calculating unit 61 includes a target condition setting section (desired condition setting section) 68. As shown in FIG. 7, a target condition (desired condition), in which ultrasonic vibrations having target amplitude (desired amplitude) are generated when a current having a predetermined value is supplied, is set by the target condition setting section 68 (step S103).

Figure 8:
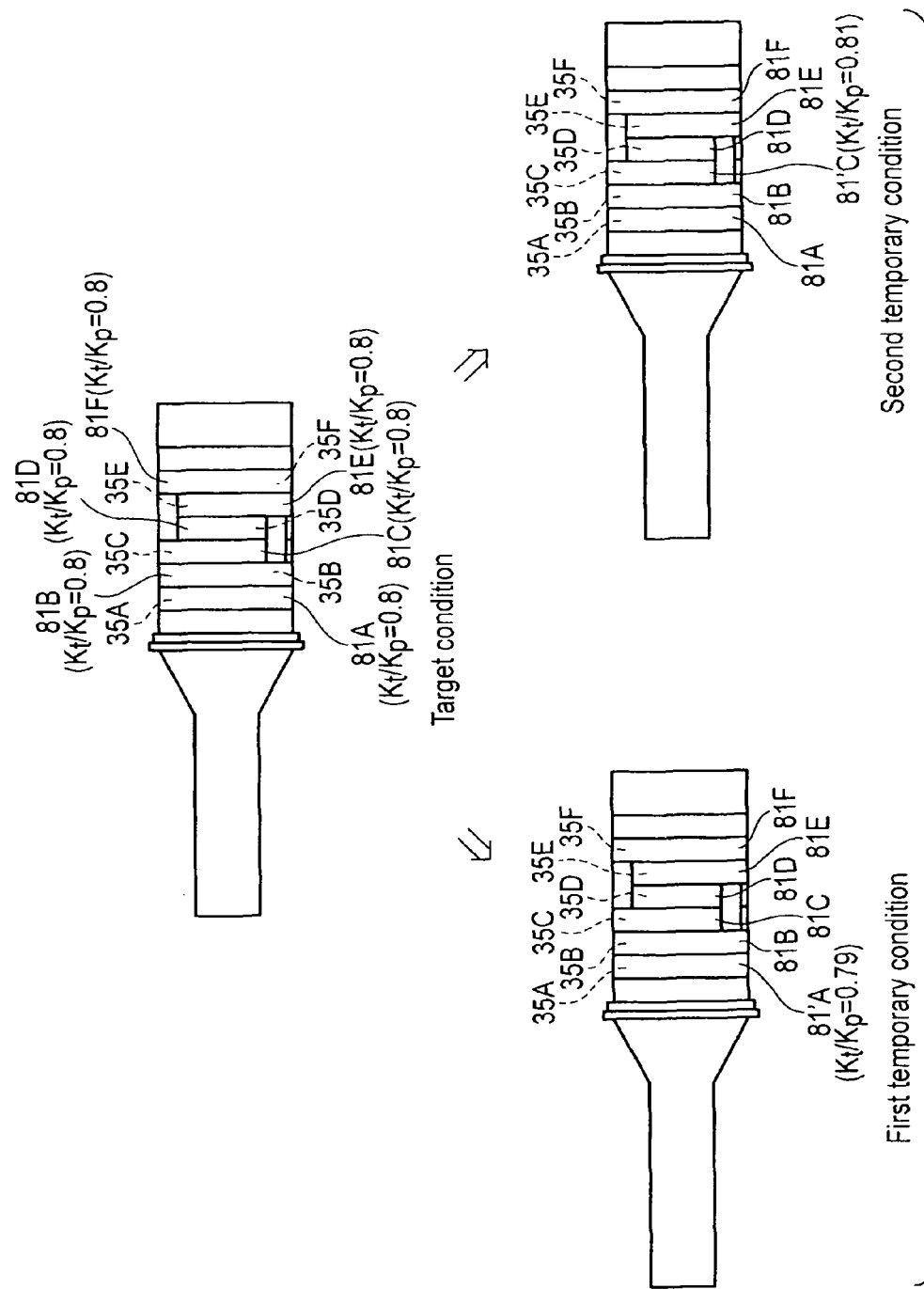
FIG. 8 is a schematic diagram showing a target condition, a first temporary condition, and a second temporary condition of each element mounting portion of the ultrasonic generating device according to the first embodiment.

FIG. 8 is a schematic diagram showing element mounting portions 35A to 35F in the target condition, a first temporary condition, and a second temporary condition (details of the target condition, the first temporary condition, and the second temporary condition will be described later). As shown in FIG. 8, a corresponding reference piezoelectric element 81A to 81F having a performance value Kt/Kp equal to a reference value is mounted on each of the element mounting portions 35A to 35F in the target condition. In the present embodiment, the performance value Kt/Kp of each of the reference piezoelectric elements 81A to 81F is a reference value of 0.8. The corresponding reference piezoelectric element 81A to 81F having the performance value Kt/Kp equal to the reference value of 0.8 is mounted on each of the element mounting portions 35A to 35F. As a result, ultrasonic vibrations having target amplitude are generated in the ultrasonic generating device 25 when the current having the predetermined current value is supplied. Here, the performance value Kt/Kp (reference value) of corresponding reference piezoelectric element 81A to 81F mounted on each of the element mounting portions 35A to 35F in the target condition is recorded in the recording section 65.

The performance values Kt/Kp (reference value) of all reference piezoelectric elements 81A to 81F are 0.8 in the present embodiment, but is not limited thereto. The target amplitude of ultrasonic vibrations to be generated by the ultrasonic generating device 25 varies, for example, according to the kind of ultrasonic treatment device 1 or its used condition. As a modification, the performance value Kt/Kp (reference value) of each of the reference piezoelectric elements 81A to 81C may be 0.7, and the performance value Kt/Kp (reference value) of each of the reference piezoelectric elements 81D to 81F may be 0.8. That is, in the target condition, it is only necessary that a corresponding reference piezoelectric element 81A to 81F having the performance value Kt/Kp equal to the reference value is mounted on each of the element mounting portions 35A to 35F and that ultrasonic vibrations having target amplitude be generated by the supply of a current having the predetermined current value.

Even when the target amplitude is the same, the reference value of each of reference piezoelectric elements 81A to 81F varies according to the predetermined current supplied from the power supply unit 7. That is, in the present embodiment, a target condition to be set varies in accordance with the performance of the selected power supply unit 7.

Here, it is considered that ultrasonic vibrations having target amplitude are generated if the performance value Kt/Kp of the corresponding piezoelectric element (mounted piezoelectric element) 33A to 33F mounted on each of the element mounting portions 35A to 35F is set at the reference value (0.8). However, when each of existing piezoelectric elements P1 to P50 is manufactured, it is not possible to set the first electromechanical coupling factor Kt in the thickness directions and the second electromechanical coupling factor Kp in the diametrical directions to desired values. Therefore, the piezoelectric element (mounted piezoelectric elements) 33A to 33F having the performance value Kt/Kp equal to the reference value (0.8) is not necessarily mounted on each of the element mounting portions 35A to 35F due to the number of the existing piezoelectric elements (P1 to P50) belonging to each of the types. For example, when the number of the existing piezoelectric elements (P1 to P50) belonging to the type having a performance value Kt/Kp of 0.8 is five or less, the piezoelectric element (33A and 33B) having the performance value Kt/Kp different from the reference value (0.8) is mounted on each of at least one element mounting portion (for example, 35A and 35B). In this case, the amplitude of the ultrasonic vibrations generated by the ultrasonic generating device 25 is different from the target amplitude.

When the ultrasonic generating device 25 is manufactured, the following processing is necessary. If the following processing is performed, the difference between the amplitude of the ultrasonic vibrations generated in each of the manufactured ultrasonic generating devices 25 and the desired amplitude is reduced. As shown in FIG. 6, the calculating unit 61 includes a temporary influence value calculating section 69. As shown in FIG. 7, a temporary influence value is calculated by the temporary influence value calculating section 69 for each of temporary conditions (step S104).

The first temporary condition and the second temporary condition are shown in FIG. 8 as examples of temporary conditions. As shown in FIG. 8, in the first temporary condition, a temporary piezoelectric element 81'A having the performance value Kt/Kp different from the reference value (0.8) is mounted on only element mounting portion 35A instead of reference piezoelectric element 81A as compared with the target condition (desired condition). The performance value Kt/Kp of the temporary piezoelectric element 81'A is 0.79. The reference piezoelectric element 81B to 81F having the performance value Kt/Kp equal to the reference value (0.8) is mounted on each of the element mounting portions 35B to 35F other than element mounting portion 35A.

In the second temporary condition different from the first temporary condition, a temporary piezoelectric element 81'C having the performance value Kt/Kp different from the reference value (0.8) is mounted on only element mounting portion 35C instead of reference piezoelectric element 81C as compared with the target condition. The performance value Kt/Kp of the temporary piezoelectric element 81'C is 0.81. The reference piezoelectric element 81A, 81B, and 81D to 81F having the performance value Kt/Kp equal to the reference value (0.8) is mounted on each of the element mounting portions 35A, 35B, and 35D to 35F other than element mounting portion 35C.

As described above, in each of the temporary conditions, a temporary piezoelectric element (for example, 81'A or 81'C) having the performance value Kt/Kp different from the reference value (0.8) is mounted on only one element mounting portion (for example, 35A or 35C) instead of the reference piezoelectric element (81A or 81C) as compared with the target condition. Therefore, in each temporary condition, ultrasonic vibrations having temporary amplitude different from the target amplitude are generated by the supply of the current having the predetermined current value. The temporary conditions are set for each of element mounting portions 35A to 35F on which the temporary piezoelectric element is mounted and for each performance value Kt/Kp of the temporary piezoelectric element.

The temporary influence value calculating section 69 is configured to calculate a temporary influence value for each temporary condition (step S104). In each temporary condition, a temporary influence value is calculated on the basis of a deviation of the temporary amplitude of the ultrasonic vibrations generated by the supply of the current having the predetermined current value from (with respect to) the target amplitude in the target condition. The temporary influence value E1(%) in the first temporary condition is as follow.

$$E1 = \frac{A1 - A0}{A0} \cdot 100 \tag{1}$$

Here, A1 is the temporary amplitude of the ultrasonic vibrations generated in, for example, the first temporary condition, and A0 is the target amplitude in the target condition. Moreover, the temporary amplitude of the ultrasonic vibrations generated in each of the temporary conditions other than the first temporary condition is Ak (k=2, 3, 4, . . . ). The temporary influence value Ek in each of the temporary conditions other than the first temporary condition is calculated by the substitution of Ak for A1 in Equation (1).

FIG. 9 is a diagram showing a table in which the temporary influence value in each of the temporary conditions is arranged. In the first temporary condition, the temporary piezoelectric element 81'A having a performance value Kt/Kp of 0.79 is mounted on only element mounting portion 35A instead of reference piezoelectric element 81A as compared with the target condition. Therefore, as shown in FIG. 9, the temporary influence value in the first temporary condition is −0.514(%). In the second temporary condition, the temporary piezoelectric element 81'C having a performance value Kt/Kp of 0.81 is mounted on only element mounting portion 35C instead of reference piezoelectric element 81C as compared with the target condition. Therefore, as shown in FIG. 9, the temporary influence value in the second temporary condition is 0.447(%).

As shown in FIG. 9, the change of the temporary influence value with respect to the change of the performance value Kt/Kp of the temporary piezoelectric element from the reference value is greater when the temporary piezoelectric element is mounted on element mounting portion 35A rather than on element mounting portion 35C. For example, the temporary influence value is −1.028(%) in the temporary condition in which the temporary piezoelectric element having a performance value Kt/Kp of 0.78 is mounted on element mounting portion 35A, whereas the temporary influence value is −0.894(%) in the temporary condition in which the temporary piezoelectric element having a performance value Kt/Kp of 0.78 is mounted on element mounting portion 35C. Here, element mounting portion 35A is less distant from the node position of the ultrasonic vibrations in the transmission direction of the ultrasonic vibrations than element mounting portion 35C. That is, the change of the temporary influence value is greater as the distance from the node position of the ultrasonic vibrations to each of element mounting portions 35A to 35F in the transmission direction of the ultrasonic vibrations is shorter.

Actually, the change of the performance values of piezoelectric elements 33A to 33F to be mounted has a greater influence on the amplitude of the ultrasonic vibrations as the distance from the node position of the ultrasonic vibrations to each of element mounting portions 35A to 35F in the transmission direction of the ultrasonic vibrations is shorter.

As shown in FIG. 6, the calculating unit 61 includes a piezoelectric element selection section 71. As shown in FIG. 7, the piezoelectric element selection section 71 is configured to each of select piezoelectric elements (mounted piezoelectric elements) 33A to 33F to be mounted on the corresponding element mounting portion 35A to 35F from existing piezoelectric elements P1 to P50 (step S105). When piezoelectric elements (mounted piezoelectric elements) 33A to 33F are selected from existing piezoelectric elements P1 to P50, in each of element mounting portions 35A to 35F, the temporary influence value in the temporary condition, in which the temporary piezoelectric element having the same performance value Kt/Kp as the corresponding piezoelectric element 33A to 33F to be actually mounted, is used as an actual influence value. For example, when piezoelectric element (mounted piezoelectric element) 33A having a performance value Kt/Kp of 0.79 is mounted on element mounting portion 35A, a temporary influence value of −0.514% in the first temporary condition (see FIG. 8) is the actual influence value of the element mounting portion 35A. When piezoelectric element (mounted piezoelectric element) 33C having a performance value Kt/Kp of 0.81 is mounted on element mounting portion 35C, a temporary influence value of 0.447% in the second temporary condition (see FIG. 8) is the actual influence value of the element mounting portion 35C.

In this way, an actual influence value of each of element mounting portions 35A to 35F is found. The piezoelectric element selection section 71 selects the corresponding piezoelectric element 33A to 33F to be mounted on each of the element mounting portions 35A to 35F so that the sum of the actual influence values (real influence values) of all element mounting portions 35A to 35F is within a predetermined range with respect to (for) the target amplitude.

For example, the corresponding piezoelectric element 33A to 33F to be mounted on each of the element mounting portion 35A to 35F is selected so that the sum of the actual influence values of all element mounting portions 35A to 35F is within a predetermined range from −2% to +2%. If the sum of the actual influence values of all element mounting portions 35A to 35F is within the range from −2% to +2%, there will be no great difference between the actual amplitude (real amplitude) of the ultrasonic vibrations and the target amplitude when a current having a predetermined value is supplied. As a result, the amplitude of ultrasonic vibrations to be generated is stable in each of the manufactured ultrasonic generating devices 25. This effectively prevents the variation of treatment performance among the ultrasonic treatment devices 1 each of which includes corresponding ultrasonic generating devices 25.

Here, the piezoelectric element selection section 71 selects piezoelectric elements 33A and 33B having a performance value Kt/Kp of 0.84, piezoelectric element 33C having a performance value Kt/Kp of 0.8, and piezoelectric elements 33D, 33E, and 33F having a performance value Kt/Kp of 0.765. In this case, the actual influence value of element mounting portion 35A is 2.056(%), the actual influence value of element mounting portion 35B is 1.922(%), the actual influence value of element mounting portion 35C is 0(%), the actual influence value of element mounting portion 35D is −1.448(%), the actual influence value of element mounting portion 35E is −1.331(%), and the actual influence value of element mounting portion 35F is −1.214(%). Thus, the sum of the actual influence values of all element mounting portions 35A to 35F is as follow.

$$2.056+1.922+0-1.448-1.331-1.214=-0.015(\%) \quad (2)$$

As the sum of the actual influence values of all element mounting portions 35A to 35F is −0.015%, ultrasonic vibrations having actual amplitude hardly different from the target amplitude are generated when the predetermined value current is supplied.

The target condition to be set varies according to the performance of the selected power supply unit 7. The actual influence value of each of the element mounting portions 35A to 35F is then calculated on the basis of the set target condition, and each of piezoelectric elements 33A to 33F is selected on the basis of the sum of the actual influence values of all element mounting portions 35A to 35F. Therefore, each of piezoelectric elements (mounted piezoelectric elements) 33A to 33F is selected in accordance with the performance of the selected power supply unit 7, for example, the predetermined current value of the current to be supplied to the ultrasonic generating device 25, and the performance of the ultrasonic generating device 25 is set. That is, the performance of the power supply unit 7 and the performance of the treatment portion 22 are not set in accordance with the performance of the ultrasonic generating device 25. Thus, it is not necessary to provide the power supply unit 7 with a control system which is configured to adjust the current value of current to be supplied to the ultrasonic generating device 25 in accordance with the performance of the ultrasonic generating device 25. Moreover, it is not necessary to select the power supply unit 7 and the treatment portion 22 which are initially set to adapt to the performance of the ultrasonic generating device 25.

The piezoelectric element selection section 71 selects each of piezoelectric elements (mounted piezoelectric elements) 33A to 33F preferential from a type including more existing piezoelectric elements among existing piezoelectric elements P1 to P50 classified into types by the piezoelectric element classification section 67 based on to the performance value Kt/Kp. For example, there are a plurality of combinations of piezoelectric elements 33A to 33F such that the sum of the actual influence values of all element mounting portions 35A to 35F is within a predetermined range with respect to the target amplitude. Moreover, the existing number of existing piezoelectric elements in the type (for example, P20 and P29) having a performance value Kt/Kp of 0.76 is a greater than other types among existing piezoelectric elements P1 to P50. In this case, a combination in which the number of existing piezoelectric elements, which belong the type having a performance value Kt/Kp of 0.76, is greater in the piezoelectric elements 33A to 33F to be mounted is selected from a plurality of combinations. That is, the piezoelectric elements are selected as each of piezoelectric elements 33A to 33F preferential from a type including more existing piezoelectric elements among existing piezoelectric elements P1 to P50 classified into types according to the performance value Kt/Kp on the condition that the sum of the actual influence values of all element mounting portions 35A to 35F is within a predetermined range with respect to the target amplitude. Consequently, piezoelectric elements (mounted piezoelectric elements) 33A to 33F are efficiently selected from existing piezoelectric elements P1 to P50 in which the existing number of existing piezoelectric elements in each of the types is different from other types.

As shown in FIG. 7, when the ultrasonic generating device 25 is manufactured, components such as the columnar portion 31 and the back-mass 53 are cleaned in parallel with steps S101 to S105 (step S106). Cleaning of the components prevents the performance deterioration of the ultrasonic generating device 25 and the ultrasonic treatment device 1 caused by, for example, dirt. The first electrode 37 and the second electrode 38 are formed by bending (step S107). As a modification, it is possible to provide no link portions 42A to 42C in the first electrode 37, and connect a corresponding electrical signal line (not shown) to each of the ring portions 41A to 41D. In this case, the first electrode 37 is not formed by bending. Similarly, it is possible to provide no link portions 46A and 46B in the second electrode 38, and connect a corresponding electrical signal line (not shown) to each of the ring portions 45A to 45C. In this case, the second electrode 38 is not formed by bending.

An adhesive material is then applied (coated) between the components (step S108). Components such as piezoelectric elements 33A to 33F selected in step S105 are then mounted on the columnar portion 31 (step S109). At this time, each of the piezoelectric elements 33A to 33F is mounted on the corresponding element mounting portion 35A to 35F. Each of the piezoelectric elements 33A to 33F is mounted so that the thickness directions are parallel to the transmission direction of the ultrasonic vibrations and so that the diametrical directions are perpendicular to the transmission direction of the ultrasonic vibrations. The back-mass 53 is then mounted (step S110). Components such as piezoelectric elements 33A to 33F are pressed toward the distal direction by the back-mass 53. As a result, piezoelectric elements 33A to 33F which are firmly fixed between the horn 27 and the back-mass 53 are mounted. The adhesive material applied in step S108 is then cured (step S111), and parts between the components are firmly bonded. Bonding may be only performed between the horn 27 and the back-mass 53 to only prevent unfastening after production.

The ultrasonic generating device 25 is manufactured as described above in steps S101 to S111. When the ultrasonic treatment device 1 is manufactured, the power supply unit 7 is electrically connected to piezoelectric elements 33A to 33F via, for example, electrical signal lines 43 and 47. The probe 19 is then coupled to the horn 27 of the ultrasonic generating device 25. As a result, the treatment portion 22, to which the ultrasonic vibrations generated by the ultrasonic generating device 25 are transmitted and which is configured to conduct a treatment by using the transmitted ultrasonic vibrations, is formed.

Accordingly, the ultrasonic generating device 25 having the configuration described above and the manufacturing method of the ultrasonic generating device 25 provide the following advantageous effects. That is, when the ultrasonic generating device 25 is manufactured, the actual influence value of each of element mounting portions 35A to 35F is found by the use of temporary influence value in the corresponding temporary condition. The piezoelectric element selection section 71 then selects each of piezoelectric elements 33A to 33F to be mounted on the corresponding element mounting portion 35A to 35F so that the sum of the actual influence values of all element mounting portions 35A to 35F is within a predetermined range (for example, −2% to +2%) with respect to the target amplitude. If the sum of the actual influence values of all element mounting portions 35A to 35F is within a predetermined range with respect to the target amplitude, there will be no great difference between the actual amplitude of the ultrasonic vibrations and the target amplitude when the current having the predetermined current value is supplied. As a result, the amplitude of ultrasonic vibrations to be generated is stable in each of the manufactured ultrasonic generating devices 25. That is, the variation of the amplitude of the ultrasonic vibrations generated in each ultrasonic generating device 25 can be reduced. This effectively prevents the difference (variation) of treatment performance among each of the ultrasonic treatment device 1 which use the corresponding ultrasonic generating devices 25.

The target condition, which is set when the ultrasound generating device 25 is manufactured, varies according to the performance of the selected power supply unit 7. The actual influence value of each of the element mounting portions 35A to 35F is then calculated on the basis of the set target condition, and each of piezoelectric elements 33A to 33F is selected on the basis of the sum of the actual influence values of all element mounting portions 35A to 35F. Therefore, each of piezoelectric elements (mounted piezoelectric elements) 33A to 33F is selected in accordance with the performance of the power supply unit 7, for example, a predetermined current value of the current to be supplied to the ultrasonic generating device 25, and the performance of the ultrasonic generating device 25 is set. That is, the performance of the power supply unit 7 and the performance of the treatment portion 22 are not set in accordance with the performance of the ultrasonic generating device 25. Thus, it is not necessary to provide the power supply unit 7 with a control system which is configured to adjust the current value of the current to be supplied to the ultrasonic generating device 25 in accordance with the performance of the ultrasonic generating device 25. Moreover, it is not necessary to select the power supply unit 7 and the treatment portion 22 which are initially set to adapt to the performance of the ultrasonic generating device 25. Therefore, the amplitude of ultrasonic vibrations to be generated can be stable regardless of the initial setting of the power supply unit 7 and the treatment portion 22 to be combined and without the complicated configuration of the power supply unit 7.

When the ultrasonic generating device 25 is manufactured, a change of the temporary influence value with respect to the change of the performance value Kt/Kp from the reference value (0.8) is calculated greater as the distance from the node position of the ultrasonic vibrations to each of element mounting portions 35A to 35F in the transmission direction of the ultrasonic vibrations is shorter. Actually, the change of the performance value of each of piezoelectric elements 33A to 33F to be mounted has a greater influence on the amplitude of the ultrasonic vibrations as the distance from the node position of the ultrasonic vibrations to each of element mounting portions 35A to 35F in the transmission direction of the ultrasonic vibrations is shorter. Therefore, the accuracy of a temporary influence value to be calculated can be enhanced.

Furthermore, when the ultrasonic generating device 25 is manufactured, the piezoelectric elements 33A to 33F are selected preferential from a type including more existing piezoelectric elements among existing piezoelectric elements P1 to P50 classified into types according to the performance value Kt/Kp, as long as the sum of the actual influence values of all element mounting portions 35A to 35F is within the predetermined range with respect to the target amplitude. Consequently, each of piezoelectric elements (mounted piezoelectric elements) 33A to 33F can be efficiently selected from existing piezoelectric elements P1 to P50 in which the existing number in each of types is different (varies) from other types.

Modifications of First Embodiment

Although the proximal end of the ultrasonic generating device 25 (the proximal end of the columnar portion 31) and the distal end of the ultrasonic generating device 25 (the distal end of the horn 27) are the anti-node positions of the ultrasonic vibrations in the first embodiment, this is not a limitation. For example, as in a first modification shown in FIG. 10, the distal end of the ultrasonic generating device 25 (the distal end of the horn 27) does not have to be the anti-node position of the ultrasonic vibrations. However, in the present modification as well, the proximal end of the ultrasonic generating device 25 (the proximal end of the columnar portion 31) and the distal end of the probe 19 are the anti-node positions of the ultrasonic vibrations.

Although the dimension of the ultrasonic generating device 25 in the transmission direction of the ultrasonic vibrations is equal to half the wavelength of the ultrasonic vibrations in the first embodiment, this is not a limitation. Moreover, the position of each of element mounting portions 35A to 35F in the transmission direction of the ultrasonic vibrations is not limited to the position in the first embodiment. For example, as in a second modification shown in FIG. 11, the dimension of the ultrasonic generating device 25 in the transmission direction of the ultrasonic vibrations may be equal to one wavelength of the ultrasonic vibrations. In the present modification, element mounting portions 82A to 82F are provided instead of element mounting portions 35A to 35F. A corresponding piezoelectric element 33A to 33F is mounted on each of the element mounting portions 82A to 82F.

In the present modification, a columnar portion 83 having a larger diameter than the columnar portion 31 is formed between element mounting portion 82A and the horn 27. Each of piezoelectric elements 33A to 33F is mounted to be fixed between the back-mass 53 and the columnar portion 83.

In the present modification as well, the temporary influence value calculating section 69 is configured to calculate each temporary influence value so that the change of the temporary influence value with respect to the change of the performance value Kt/Kp from the reference value is greater as the distance from the node position of the ultrasonic vibrations to each of element mounting portions 82A to 82F in the transmission direction of the ultrasonic vibrations is shorter. For example, the distance from the node position of the ultrasonic vibrations to each of element mounting portions 82B and 82E in the transmission direction of the ultrasonic vibrations substantially coincides with the distance from the node position of the ultrasonic vibrations to element mounting portion 35A in the transmission direction of the ultrasonic vibrations in the first embodiment. Thus, the change of the temporary influence value in each of element mounting portions 82B and 82E with respect to the change of the performance value Kt/Kp from the reference value show substantially the same characteristics as the change of the temporary influence value in element mounting portion 35A in response to the change of the performance value Kt/Kp from the reference value (see FIG. 9).

For example, as in a third modification shown in FIG. 12, the dimension of the ultrasonic generating device 25 in the transmission direction of the ultrasonic vibrations may be equal to one wavelength of the ultrasonic vibrations, and element mounting portions 85A to 85F may be provided instead of element mounting portions 35A to 35F. In the present modification, a cylindrical member 86 is provided (mounted) between element mounting portion 85B and element mounting portion 85C. Each of piezoelectric elements 33A to 33F and the cylindrical member 86 are mounted to be fixed between the back-mass 53 and the horn 27.

In the present modification as well, the temporary influence value calculating section 69 is configured to calculate each temporary influence value so that the change of the temporary influence value with respect to the change of the performance value Kt/Kp from the reference value is greater as the distance from the node position of the ultrasonic vibrations to each of element mounting portions 85A to 85F in the transmission direction of the ultrasonic vibrations is shorter. For example, the distance from the node position of the ultrasonic vibrations to each of element mounting portions 85A, 85C, and 85F in the transmission direction of the ultrasonic vibrations substantially coincide with the distance from the node position of the ultrasonic vibrations to element mounting portion 35A in the transmission direction of the ultrasonic vibrations in the first embodiment. Thus, the change of the temporary influence value in each of element mounting portions 85A, 85C, and 85F with respect to the change of the performance value Kt/Kp from the reference value show substantially the same characteristics as the change of the temporary influence value in element mounting portion 35A with respect to the change of the performance value Kt/Kp from the reference value (see FIG. 9).

For example, as in a fourth modification shown in FIG. 13, the dimension of the ultrasonic generating device 25 in the transmission direction of the ultrasonic vibrations may be equal to 1.5 wavelengths of the ultrasonic vibrations. In the present modification, eight element mounting portions 91A to 91H are provided instead of element mounting portions 35A to 35F. A corresponding piezoelectric element (mounted piezoelectric element) 33A to 33H is mounted on each of the element mounting portions 91A to 91H. In the present modification, a columnar portion 92 having a larger diameter than the columnar portion 31 is formed between element mounting portion 91A and the horn 27. A cylindrical member 93 is mounted between element mounting portion 91D and element mounting portion 91E. Each of piezoelectric elements 33A to 33H and the cylindrical member 93 are mounted to be fixed between the back-mass 53 and the columnar portion 92.

In the present modification as well, the temporary influence value calculating section 69 is configured to calculate each temporary influence value so that the change of the temporary influence value with respect to the change of the performance value Kt/Kp from the reference value is greater as the distance from the node position of the ultrasonic vibrations to each of element mounting portions 91A to 91H in the transmission direction of the ultrasonic vibrations is shorter. For example, the distance from the node position of the ultrasonic vibrations to each of element mounting portions 91A, 91D, 91E, and 91H in the transmission direction of the ultrasonic vibrations substantially coincides with the distance from the node position of the ultrasonic vibrations to element mounting portion 35A in the transmission direction of the ultrasonic vibrations in the first embodiment. Thus, the change of the temporary influence value in each of element mounting portions 91A, 91D, 91E, and 91H with respect to the change of the performance value Kt/Kp from the reference value show substantially the same characteristics as the change of the temporary influence value in element mounting portion 35A with respect to the change of the performance value Kt/Kp from the reference value (see FIG. 9).

Figure 14:
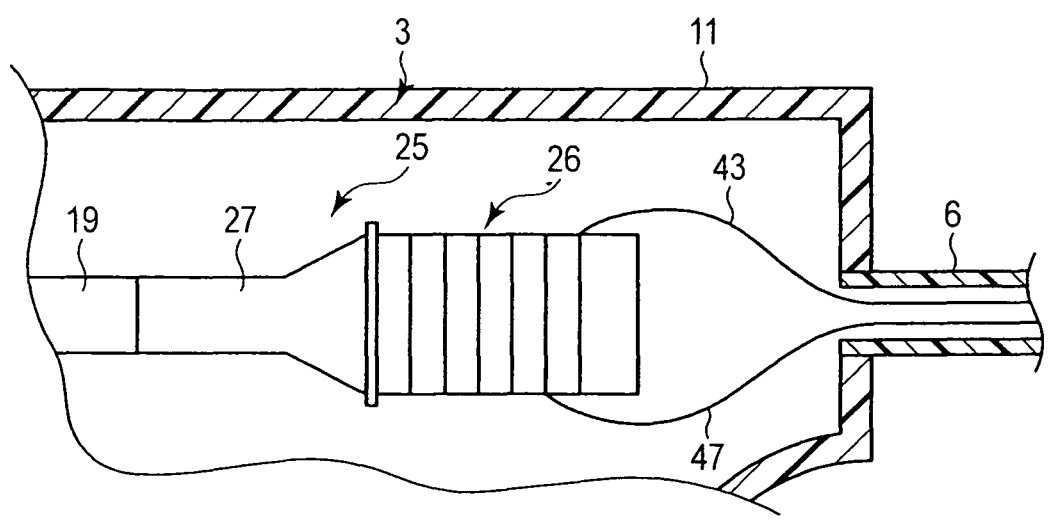
FIG. 14 is a schematic sectional view showing the internal configuration of a handle unit of an ultrasonic treatment device according to a fifth modification of the first embodiment.

Although the ultrasonic generating device 25 is provided inside the vibrator case 23 in the ultrasonic treatment device 1 according to the first embodiment, this is not a limitation. For example, as in a fifth modification shown in FIG. 14, no vibrator case 23 may be provided. In the present modification, the ultrasonic generating device 25 is provided inside the cylindrical case 11 of the handle unit 3. One end of the cable 6 is connected to the cylindrical case 11. Electrical signal lines 43 and 47 each of which has one end connected to the ultrasonic generating device 25, and the other end connected to the power supply unit 7 through an inside of the cylindrical case 11 and an inside of the cable 6.

Other characteristic technical matters according to the present invention are additionally set forth below.

Notes (Additional Note 1)

An ultrasonic adjusting device comprising:

a plurality of element mounting portions located at positions different from one another in a transmission direction of ultrasonic vibrations;

a plurality of existing piezoelectric elements including mounted piezoelectric elements each of which is mounted on a corresponding element mounting portion so that thickness directions thereof are parallel to the transmission direction of the ultrasonic vibrations and so that diametrical directions thereof are perpendicular to the transmission direction of the ultrasonic vibrations;

a performance value calculating section which is configured to calculate a performance value based on a first electromechanical coupling factor in the thickness directions and a second electromechanical coupling factor in the diametrical directions for each of the existing piezoelectric elements;

a target condition setting section which is configured to set a target condition where the ultrasonic vibrations having target amplitude are generated when a corresponding reference piezoelectric element having the performance value equal to a reference value is mounted on each of the element mounting portions and when a current having a predetermined current value is supplied;

a temporary influence value calculating section which is configured to calculate, for each of temporary conditions; a temporary influence value on the basis of a deviation of temporary amplitude of the ultrasonic vibrations, generated by the supply of the current having the predetermined current value, from the target amplitude in the target condition, a temporary piezoelectric element having the performance value different from the reference value being mounted on only one element mounting portion instead of the reference piezoelectric element in each of the temporary conditions as compared with the target condition, and the temporary conditions being set for each of the element mounting portions on which the temporary piezoelectric element is mounted and for each of the performance values of the temporary piezoelectric elements; and a piezoelectric element selection section which is configured to select the corresponding mounted piezoelectric elements to be mounted on each of the element mounting portions from the existing piezoelectric elements so that a sum of an actual influence values of all the element mounting portions is within a predetermined range with respect to the target amplitude, when the temporary influence value in the corresponding temporary condition, in which the temporary piezoelectric element having the same performance value as the mounted piezoelectric element to be actually mounted is mounted, is used as the actual influence value in each of the element mounting portions.

(Additional Note 2)

The ultrasonic adjusting device according to additional note 1, wherein the temporary influence value calculating section is configured to calculate the temporary influence value so that a change of the temporary influence value with respect to a change of the performance value from the reference value is greater as a distance from a node position of the ultrasonic vibrations to each of the element mounting portions in the transmission direction of the ultrasonic vibrations is shorter.

(Additional Note 3)

The ultrasonic adjusting device according to additional note 1, wherein the piezoelectric element selection section is configured to select the mounted piezoelectric elements preferential from a type including more existing piezoelectric elements among the existing piezoelectric elements classified into types according to the performance value on the condition that the sum of the actual influence values of all the element mounting portions is within the predetermined range with respect to the target amplitude.

(Additional Note 4)

A manufacturing method of an ultrasonic generating device formed by mounting each of a plurality of piezoelectric elements at corresponding mounting position, the manufacturing method comprising:

calculating performance value for each of the piezoelectric elements on a basis of an electromechanical coupling factor in thickness directions and an electromechanical coupling factor in a spreading direction;

calculating, for each of the performance values, an influence value with respect to target amplitude at each of the mounting positions of the piezoelectric elements; and selecting the piezoelectric elements so that a total of the influence values is within a predetermined range, and mounting the piezoelectric elements.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A manufacturing method of an ultrasonic generating device, the manufacturing method comprising:
calculating performance value based on a first electromechanical coupling factor in thickness directions and a second electromechanical coupling factor in diametrical directions for each of existing piezoelectric elements;
setting a target condition where ultrasonic vibrations having target amplitude are generated when a corresponding reference piezoelectric element having the performance value equal to a reference value is mounted on each of a plurality of element mounting portions located at positions different from one another in a transmission direction of the ultrasonic vibrations and when a current having a predetermined current value is supplied;
calculating, for each of temporary conditions, a temporary influence value on the basis of a deviation of temporary amplitude of the ultrasonic vibrations, generated by the supply of the current having the predetermined current value, from the target amplitude in the target condition, a temporary piezoelectric element having the performance value different from the reference value being mounted on only one element mounting portion instead of the reference piezoelectric element in each of the temporary conditions as compared with the target condition, the temporary conditions being set for each of the element mounting portions on which the temporary piezoelectric element is mounted and for each of the performance values of the temporary piezoelectric elements;
selecting the corresponding mounted piezoelectric element to be mounted on each of the element mounting portions from the existing piezoelectric elements so that the sum of actual influence values of all the element mounting portions is within a predetermined range with respect to the target amplitude, when the temporary influence value in the corresponding temporary condition, in which the temporary piezoelectric element having the same performance value as the mounted piezoelectric element to be actually mounted is mounted, is used as the actual influence value in each of the element mounting portions; and
mounting the selected corresponding mounted piezoelectric elements on each of the element mounting portions so that the thickness directions thereof are parallel to the transmission direction of the ultrasonic vibrations and so that the diametrical directions thereof are perpendicular to the transmission direction of the ultrasonic vibrations.

2. The manufacturing method of the ultrasonic generating device according to claim 1, wherein the calculating the temporary influence value for each of the temporary conditions includes calculating the temporary influence value so that a change of the temporary influence value with respect to a change of the performance value from the reference value is greater as a distance from a node position of the ultrasonic vibrations to each of the element mounting portions in the transmission direction of the ultrasonic vibrations is shorter.

3. The manufacturing method of the ultrasonic generating device according to claim 1, wherein the selecting the corresponding mounted piezoelectric element to be mounted on each of the element mounting portions includes selecting the mounted piezoelectric elements preferential from a type including more existing piezoelectric elements among the existing piezoelectric elements classified into types according to the performance value on the condition that the sum of the actual influence values of all the element mounting portions is within the predetermined range with respect to the target amplitude.

4. A manufacturing method of an ultrasonic treatment device, the manufacturing method comprising:
forming the ultrasonic generating device by the manufacturing method according to claim 1;
electrically connecting a power supply unit, configured to supply the current having the predetermined current value to the ultrasonic generating device, to the mounted piezoelectric elements; and
forming a treatment portion to which the ultrasonic vibrations generated by the ultrasonic generating device are transmitted, and which is configured to conduct a treatment by using the transmitted ultrasonic vibrations.

5. A manufacturing method of an ultrasonic generating device, the manufacturing method comprising:
calculating performance value based on a first electromechanical coupling factor in thickness directions and a second electromechanical coupling factor in diametrical directions for each of piezoelectric elements;
setting, as a target amplitude, amplitude of ultrasonic vibrations generated when the corresponding piezoelectric element having the performance value equal to a reference value is mounted on each of a plurality of element mounting portions located at positions different from one another in a transmission direction of the ultrasonic vibrations and when a current having a predetermined current value is supplied;
calculating an influence value for each of the element mounting portions and for each of performance values of the piezoelectric elements, the influence value being based on a deviation of amplitude of the ultrasonic vibrations, generated by the supply of the current having the predetermined current value in a state that the piezoelectric element having the performance value different from the reference value is mounted, from the target amplitude in the target condition;
selecting the corresponding piezoelectric element to be mounted on each of the element mounting portions from all the piezoelectric elements so that a sum of the influence values of all the element mounting portions is within a predetermined range with respect to the target amplitude; and
mounting the selected corresponding piezoelectric element on each of the element mounting portions so that the thickness directions are parallel to the transmission direction of the ultrasonic vibrations and so that the diametrical directions are perpendicular to the transmission direction of the ultrasonic vibrations.

6. The manufacturing method of the ultrasonic generating device according to claim 5, wherein the calculating influence value for each of the element mounting portions on which the corresponding piezoelectric element is mounted and for each of performance values of the piezoelectric elements includes calculating the influence value so that a change of the influence value with respect to a change of the performance value from the reference value is greater as a distance from a node position of the ultrasonic vibrations to each of the element mounting portions in the transmission direction of the ultrasonic vibrations is shorter.

7. The manufacturing method of an ultrasonic generating device according to claim 5, wherein the selecting the corresponding piezoelectric element to be mounted on each of the element mounting portions includes selecting the mounted piezoelectric elements preferential from a type including more existing piezoelectric elements among the piezoelectric elements classified into types according to the performance value on the condition that the sum of the influence values of all the element mounting portions in within the predetermined range with respect to the target amplitude.

\* \* \* \* \*